United States Patent [19]

Kensey et al.

[11] Patent Number: 5,021,059
[45] Date of Patent: Jun. 4, 1991

[54] PLUG DEVICE WITH PULLEY FOR SEALING PUNCTURES IN TISSUE AND METHODS OF USE

[75] Inventors: Kenneth Kensey, Chester Springs; John Nash, Downingtown; Douglas Evans, King of Prussia, all of Pa.

[73] Assignee: Kensey Nash Corporation, Exton, Pa.

[21] Appl. No.: 519,622

[22] Filed: May 7, 1990

[51] Int. Cl.⁵ ................. A61B 17/00; A61F 13/20; A61M 31/00
[52] U.S. Cl. ................................ 606/213; 604/60; 604/15; 606/232
[58] Field of Search ............... 606/213, 232, 220, 144, 606/139, 151, 148; 604/15, 60, 288, 218, 158, 159, 167

[56] References Cited

U.S. PATENT DOCUMENTS

| | | | |
|---|---|---|---|
| 3,675,639 | 7/1972 | Cimber | 604/60 |
| 3,874,388 | 4/1975 | King et al. | 606/232 |
| 4,543,086 | 9/1985 | Johnson | 604/15 |
| 4,614,182 | 9/1986 | Boebel | 604/15 |
| 4,669,473 | 6/1987 | Richards et al. | 606/220 |
| 4,744,364 | 5/1988 | Kensey | 604/15 |
| 4,852,568 | 8/1989 | Kensey | 604/213 |
| 4,890,612 | 1/1990 | Kensey | 606/213 |

FOREIGN PATENT DOCUMENTS 0246836 11/1987 European Pat. Off. ............ 606/148

Primary Examiner—Stephen C. Pellegrino
Assistant Examiner—Gary Jackson
Attorney, Agent, or Firm—Caesar, Rivise, Bernstein, Cohen & Pokotilow, Ltd.

[57] ABSTRACT

An instrument, a closure, and method of use for sealing an opening, e.g., a percutaneous incision or puncture, in a living being. The instrument includes a tubular carrier storing the closure. The carrier has a distally located free end to be extended through the opening. The closure comprises an anchoring portion, a sealing portion and a thin filament connected therebetween. The instrument is operated to eject the anchoring portion of the closure through the incision or puncture and to then draw that portion against the free end of the carrier. The instrument is then withdrawn to pull the anchoring portion of the closure against the tissue contiguous with the incision or puncture. Further withdrawing of the instrument draws the sealing portion of the closure out of the carrier, whereupon it moves with respect to the anchoring portion and into engagement with the tissue contiguous with the opening on the opposite side of the anchoring portion to seal it. Signals are produced to indicate proper operation.

55 Claims, 4 Drawing Sheets

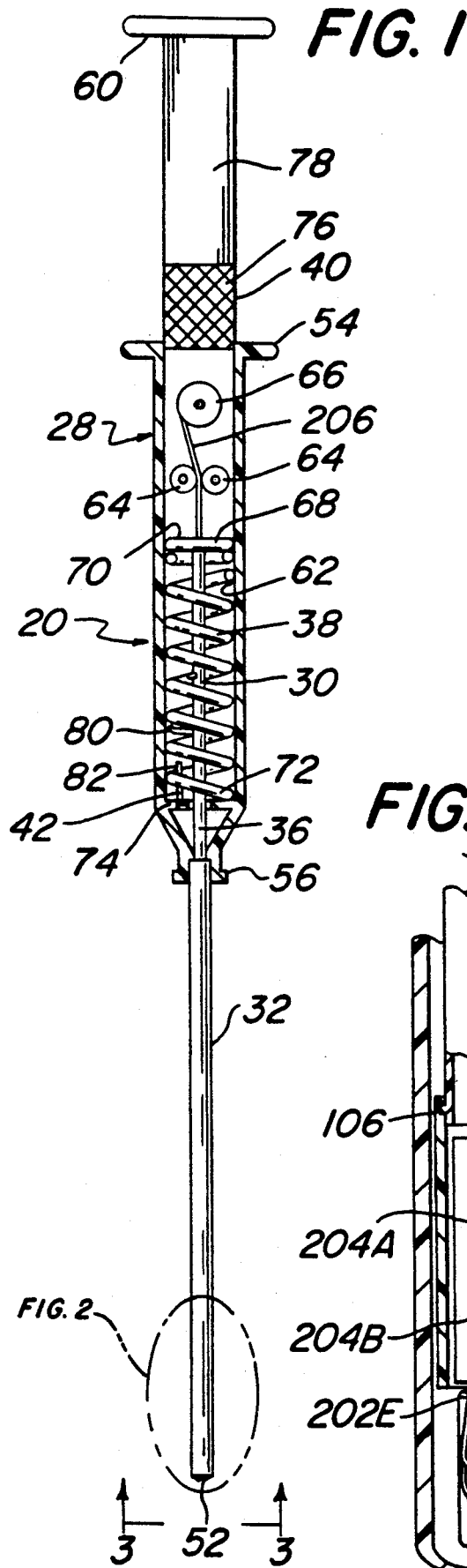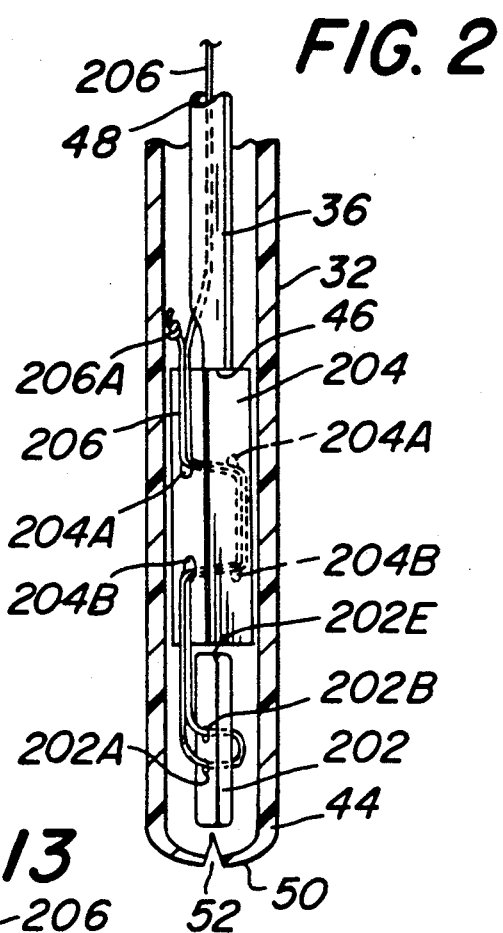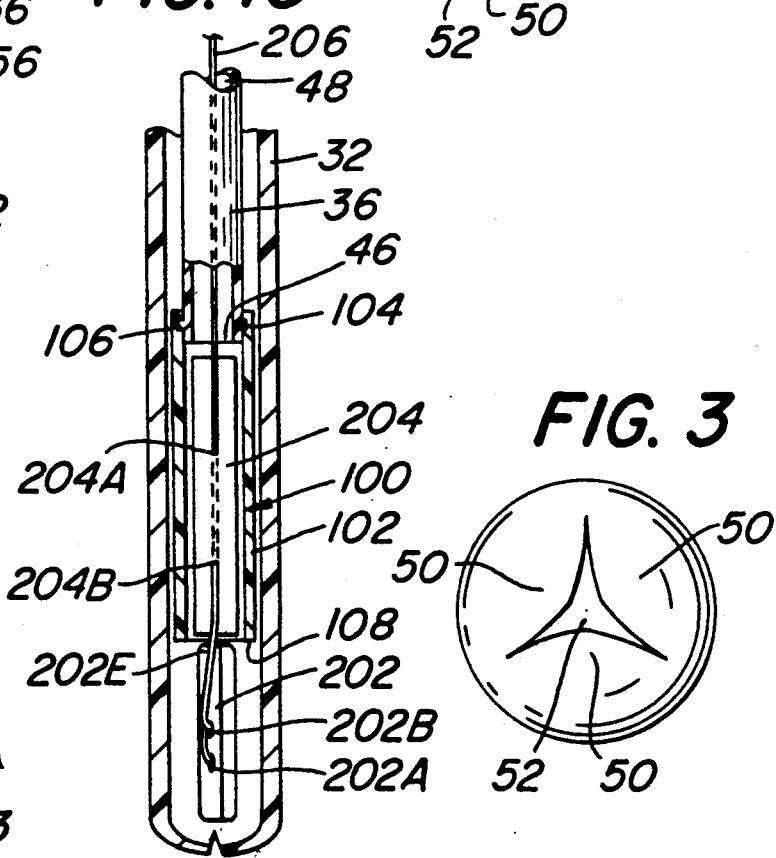

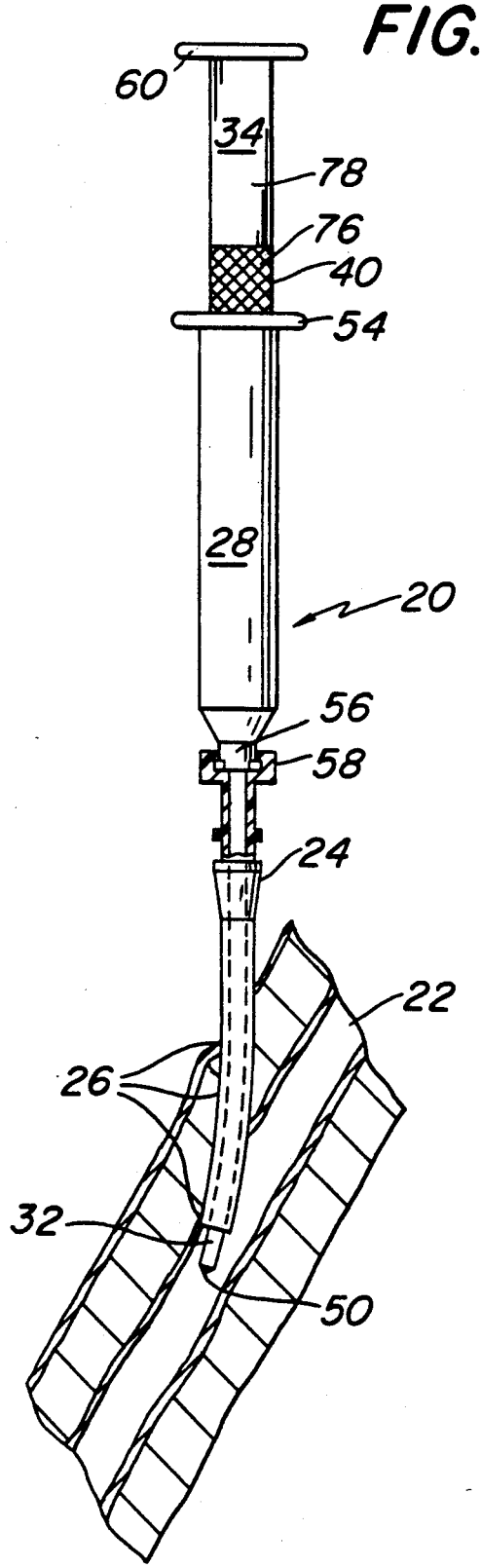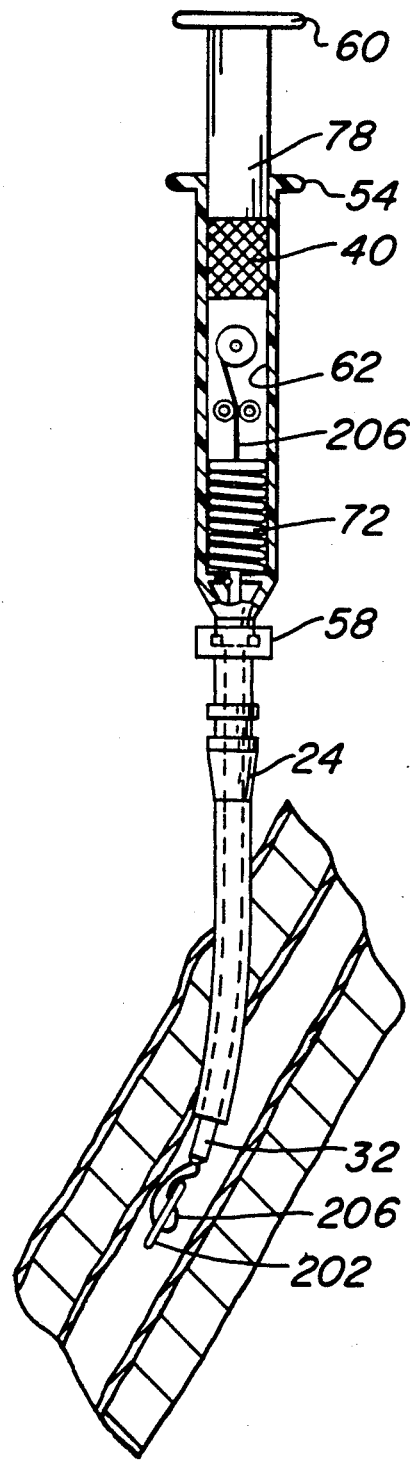

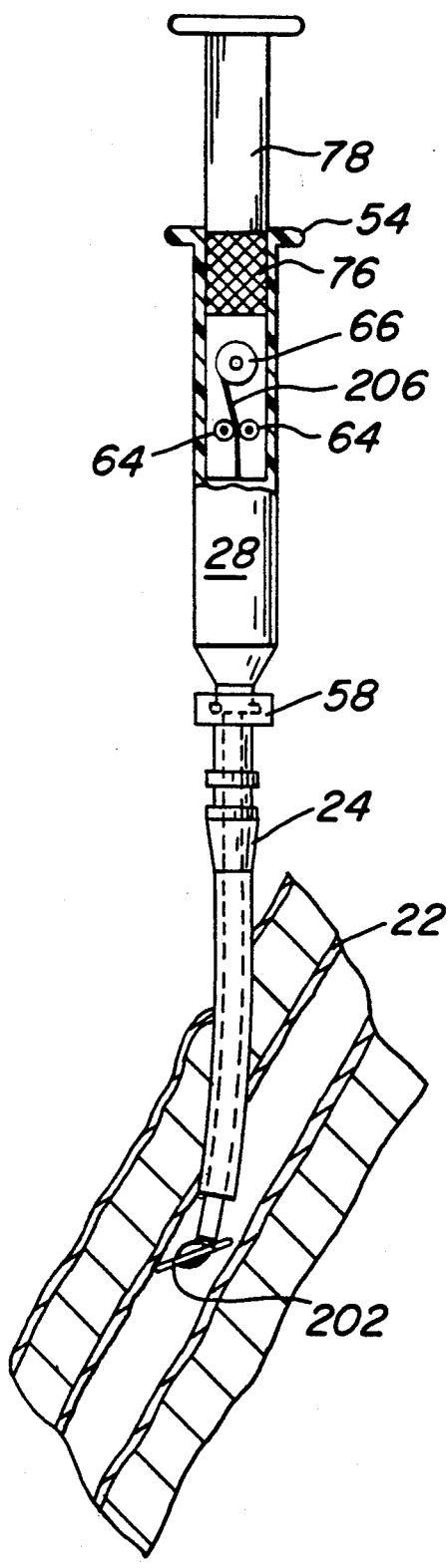
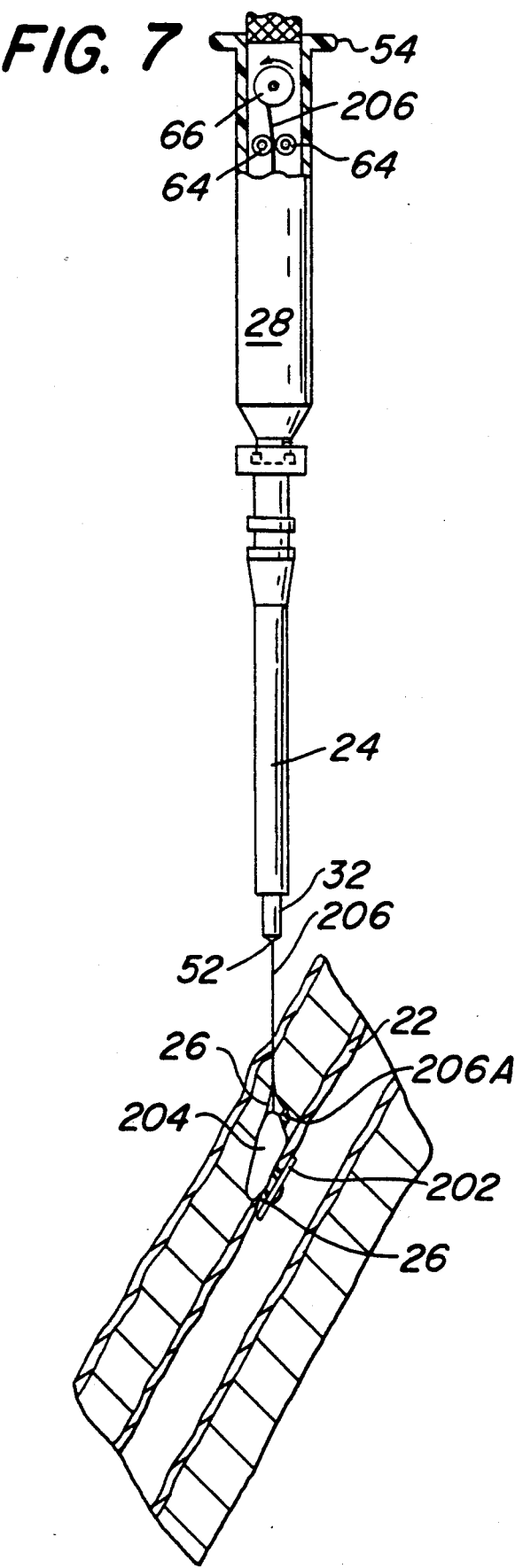

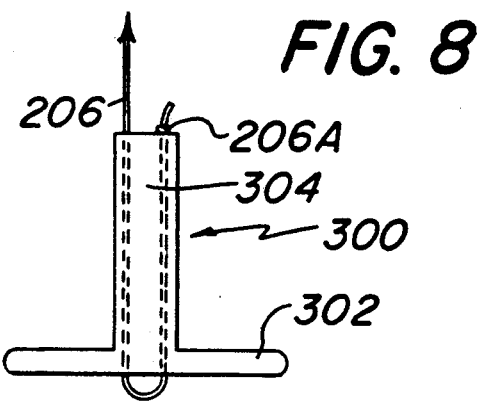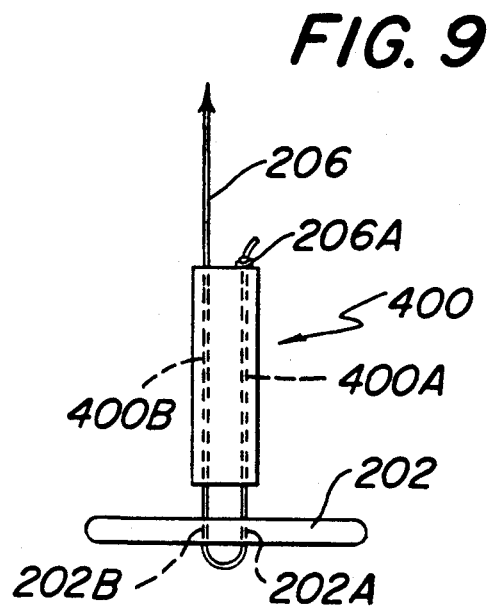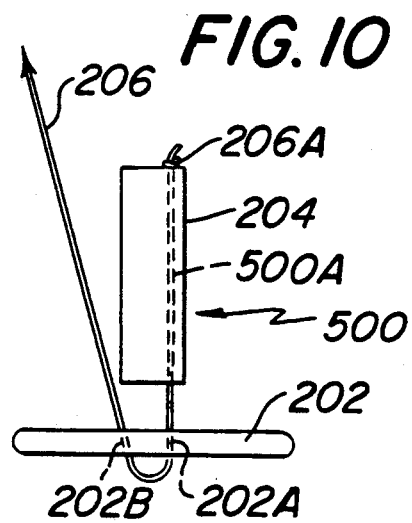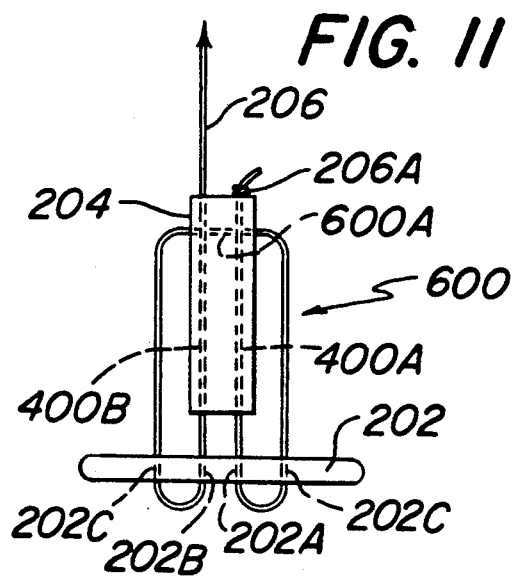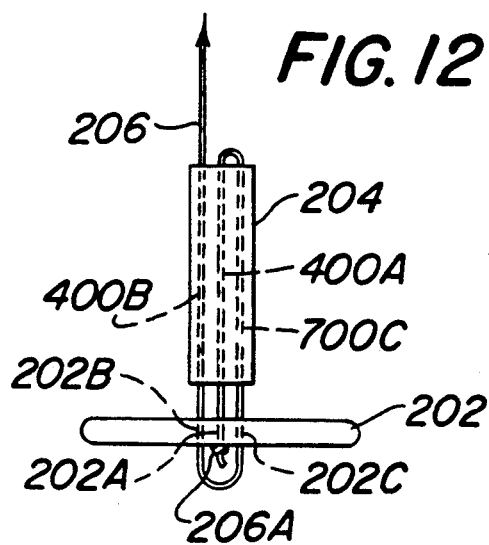

PLUG DEVICE WITH PULLEY FOR SEALING PUNCTURES IN TISSUE AND METHODS OF USE

This invention relates generally to medical devices and methods of use, and more specifically to devices and methods of use for sealing punctures or incisions in the body of a living being.

BACKGROUND OF THE INVENTION

In U.S. Pat. Nos. 4,744,364 and 4,852,568, assigned to the same assignee as this invention, there is disclosed an instrument and closure (plug) device for sealing an opening in tissue separating one portion of the body of a living being from another portion, e.g., a puncture in a blood vessel, duct or lumen, of a living being. Also disclosed are methods of use of that device. The instrument basically comprises an elongated tubular body having an outlet at its distal end. The distal end of the device is arranged to be inserted, such as percutaneously, through the puncture. In the case where the puncture is an artery or other blood vessel, the outlet is inserted through the puncture so that it is located within the blood vessel's interior. An expandable closure is disposed within the device's tubular body and is formed so that it is held in a compact or compressed configuration within the tubular body. The tubular body also includes an ejector in the form of a plunger-like member arranged to force the closure out of the outlet into the portion of the being's body contiguous with the opening, e.g., within the interior of the blood vessel, whereupon the closure automatically expands to form an enlarged tissue engagement surface.

A retraction filament is secured to the closure to enable it to be pulled fully into the puncture after the device's tubular body has been withdrawn so that the engagement surface of the closure intimately engages the inner surface of the tissue contiguous with the puncture.

In accordance with one aspect of the disclosure of those patents, the filament is held taut or otherwise secured and placed on the patient's skin to hold the closure in position in the puncture. Preferably, the closure and filament are each formed of some biodegradable material to enable them to be left in place. When the closure is used for sealing punctures or incisions in blood vessels it is constructed so that when it is open (i.e., in its expanded state) and in place sealing the puncture it doesn't appreciably block the flow of blood through the blood vessel.

In co-pending U.S. patent application, Ser. No. 194,641, filed on May 16, 1988, entitled Device For Sealing Percutaneous Puncture In A Vessel, which has been assigned to the same assignee as this invention there is disclosed another closure device for sealing a puncture or incision formed percutaneously in tissue separating two internal portions of the body of a living being and a method of use of that device. That closure also comprises plug. However, that plug is formed of a material which when located within the puncture or incision expands automatically to engage the tissue contiguous therewith to seal the puncture and incision from the flow of body fluid therethrough. The closure is in the form of a holding member, a filament, and a sealing member. The holding member is an elongated body, constructed like a toggle, and preferably formed of a biodegradable, thermoplastic polymer, such as polyglactide. The toggle is molded onto the distal end of the filament. The filament is also biodegradable, and preferably formed of polyglactide suture. The filament, being flexible, enables the toggle to pivot to various orientations with respect to it. The sealing member basically comprises a cylindrical plug, preferably formed of a compressed foam, which is highly absorbent and which when disposed within the body swells in excess of its compressed diameter.

The closure is arranged to be used by an instrument to place it within the puncture or incision to be sealed. The instrument includes a tubular member in which the closure is disposed so that the toggle is oriented with its longitudinal axis parallel to the longitudinal axis of the tubular member. When so disposed the toggle compresses the portion of the distal end of the sealing member. The filament extends backward from the toggle through the sealing member.

The instrument is introduced into the puncture or incision in the artery or any body tissue (e.g., the liver, gall bladder, lung, heart, etc.) until its outlet is at the desired position. In the case of sealing an artery, the outlet of the instrument is positioned so that it is within the artery. The instrument is then operated to expel the closure member from the tubular member. Once the closure is expelled, the instrument is held in this position for a short period of time to allow the foam at the tip of the closure, that is the distal end portion of the closure, to swell. This action effectively tilts the toggle. The instrument may then be withdrawn and the closure's filament retracted. This action pulls the closure's plug portion back through the puncture or incision in the artery wall until its toggle portion engages the inner surface of the artery wall to stop further retraction. As the toggle comes into engagement with the arterial wall, it effects the compression of the distal end portion of the sealing member. Moreover, the proximal end portion of the sealing member extends into the puncture or incision in the subcutaneous tissue to a point closely adjacent the skin. These actions effectively seal the puncture or incision from the passage of blood therethrough. Other alternative embodiments of the automatically expanding plug are also disclosed in that patent application.

In co-pending U.S. patent application, Ser. No. 445,315, filed on Dec. 4, 1989, entitled Plug Device For Sealing Openings and Method of Use, assigned to the same assignee as this invention there is disclosed yet another closure (plug) device for use with an instrument for sealing a puncture or incision in tissue separating two internal portions of the body of a living being and a method of use of that device. That device basically comprises a closure or plug made up of a cordlike member and a thin filament. The cord-like member comprises a resorbable material and is folded in two to form an apex portion and a pair of wing portions extending therefrom. The plug's filament is secured to the apex portion. The plug is arranged for location within the instrument so that its apex portion is disposed adjacent the instrument's free end, and with its wing portions and its filament extending toward the proximally located portion of the instrument. The plug is arranged to be expelled partially from the tubular free end of the instrument so that its apex portion extends through the opening. After that is accomplished the filament is drawn in the proximal direction to cause the apex portion to engage the free end of the instrument to cause the cord-like member to form an expanded head having a peripheral, tissue-engagement surface. The plug is then drawn back through the opening so that the peripheral tissue engagement surface intimately engages the tissue contiguous with the opening.

While the closures (plugs) of the aforementioned patent applications are generally suitable for their intended purposes, they nevertheless exhibit certain drawbacks.

In U.S. Pat. No. 3,874,388 (King et al.) there is disclosed a device for closing off a septal defect or shunt in the vascular system of a living being. The device includes a pair of stainless steel, umbrella-like closures which are placed in position via use of a catheter. To that end one umbrella-like closure is inserted through the septal defect (opening) by one portion of the catheter and is expanded and pulled back into engagement with the tissue surrounding the opening on one side of the septum. The other closure is then introduced, expanded and then pushed into place by another portion of the catheter so that it is on the opposite side of the septum and engaging the tissue on that side of the septum.

The closure and catheter of the King et al. patent, appear quite complex in construction and not suitable for sealing various types of openings, e.g., small incisions or punctures in tissue, such as arteries, etc.

In Russian Patent No. 782,814 there is disclosed a prosthesis device arranged to be inserted through a defect (opening) in the septum of a living being. That device includes a one-piece resilient body having a reinforcement ring and a flat spring disposed within it. The spring member is arranged to be actuated by a rod to cause it to expand to the diameter of the ring and thereby bring the resilient body into sealing engagement with the opening.

The closure of the Russian patent appears to suffer from the same disadvantages as the King et al. patent.

OBJECTS OF THE INVENTION

Accordingly, it is a general object of this invention to provide a device and methods of use which overcomes the disadvantages of the prior art.

It is a further object of this invention to provide an instrument, a closure therefore, and method of use for quickly, easily, and effectively sealing a puncture or incision in tissue separating one portion of the body of a living being from another portion.

It is a further object of this invention to provide a closure for sealing and opening in the body of a living being which is simple in construction, low in cost, and which may be left in place after its use.

It is still a further object of this invention to provide an instrument which includes various safety features for ensuring safe and proper placement of a closure into the body of a living being to seal an opening therein.

SUMMARY OF THE INVENTION

These and other objects of this invention are achieved by providing an instrument, a closure, and method of use for sealing an opening, e.g., a small opening, in tissue separating one portion of the body of a living being from another portion thereof to prevent the flow of body fluids from the one portion to the other portion through the opening.

The instrument comprises carrier means for receipt of the closure. The closure arranged to be expelled from the carrier means. The carrier means comprises a tubular member having a proximally located portion and a distally located portion. The distally located portion has a free end arranged to be introduced through the opening.

The closure comprises anchoring means, sealing means, and filament means. The anchoring means includes a tissue engaging portion configured to pass through the opening in one direction, but resistant to passage therethrough in the opposite direction. The sealing means includes a tissue engaging portion. The filament means is connected between the anchoring means and the sealing means and comprises a first portion and a second portion.

The method of use of the instrument and the closure entails locating the closure within the carrier means adjacent the free end. The free end of the carrier means is introduced through the opening and the anchoring means of the closure is expelled from the free end of the carrier means. Thereafter the instrument is operated to draw the tissue engaging portion of the anchoring means into engagement with the tissue contiguous with the opening. A drawing force is then applied on the first portion of the filament means to cause the second portion of the filament means to move the sealing means out of the carrier means, whereupon the tissue engaging portion of the sealing means moves with respect to the anchoring means and into engagement with the tissue contiguous with the opening on the opposite side from the anchoring means so that the tissue engaging portion of the sealing means seals the opening from the flow of fluid therethrough.

BRIEF DESCRIPTION OF THE DRAWINGS

Other objects and many of the attendant advantages of this invention will readily be appreciated as the same becomes better understood by reference to the following detailed description when considered in connection with the accompanying drawings wherein:

FIG. 1 is a side elevational view, partially in section, of an instrument constructed in accordance with this invention for introducing a closure constructed in accordance with this invention into the body of a living being to seal an opening therein;

FIG. 2 is an enlarged sectional view of the portion of the instrument shown in the encircled area of FIG. 1 and showing one embodiment of the closure of this invention located therein;

FIG. 3 is an enlarged end view taken along line 3—3 of FIG. 1;

FIG. 4 is a side elevational view showing an initial step in the operation of the instrument;

FIG. 5 is a side elevational view showing a later step in the operation of the instrument;

FIG. 6 is a side elevational view showing a still later step in the operation of the instrument;

FIG. 7 is a side elevational view showing a still later step in the operation of the instrument;

FIG. 8 is a side elevational view of an alternative embodiment of the closure of this invention;

FIG. 9 is a side elevational view of another alternative embodiment of the closure of this invention;

FIG. 10 is a side elevational view of yet another alternative embodiment of the closure of this invention;

FIG. 11 is a side elevational view of still another alternative embodiment of the closure of this invention;

FIG. 12 is a side elevational view of still a further alternative embodiment of the closure of this invention; and FIG. 13 is an enlarged sectional, like FIG. 2, but showing the distal end of an alternative embodiment of a portion of the instrument of FIG. 1.

DETAILED DESCRIPTION OF THE PREFERRED EMBODIMENT

Referring now in greater detail to the various figures of the drawings wherein like reference characters refer to like parts, an instrument embodying one aspect of the present invention is generally shown at 20 in FIG. 1. The instrument 20 is arranged to be used with a closure constructed in accordance with another aspect of this invention to effect the sealing of an opening, e.g., a percutaneous incision or puncture, in any tissue separating two portions of the body of a living being to prevent liquid(s) or body fluid(s) from flowing through the incision or puncture.

One embodiment of the closure of this invention is shown in FIG. 2 and is designated by the reference numeral 200. Various other embodiments of the closure are shown in FIGS. 8-12, and are designated by the reference numerals 300, 400, 500, 600 and 700.

The instrument 20 and closures 200-700 have particular utility when used in connection with intravascular procedures, such as angiographic dye injection, balloon angioplasty and other types of recanalizing of athrosclerotic arteries, etc. However, it is to be understood that while the description of the preferred embodiment instrument and closure contained herein is directed to the closing off of percutaneous incisions or punctures in arteries, they have much more wide-spread applications. Thus, the sealing of a percutaneous opening in an artery shown herein is merely exemplary.

Before describing the closure 200 and the instrument 20 for inserting it to seal the opening, a brief description of a typical, conventional, intravascular surgical procedure, e.g., catheter instrumentation of an artery, utilizing a percutaneous opening will be given to best appreciate the features of the invention. In such a procedure a cannula of an instrument, such as an angiographic needle (not shown), is inserted percutaneously through the skin into the artery, such as the femoral artery 22, at the situs for the instrument's insertion. The needle cannula is held in place and the flexible end of a mini-guidewire (not shown) is then passed through the cannula into the artery to the desired depth (i.e., longitudinal position therealong). Once the mini-guide wire is in place the needle cannula is removed, leaving the guidewire in place. An introducing sheath 24 and an arterial dilator (not shown) are then passed over the guidewire, through the puncture or incision 24 and into the artery 22. The guidewire and then the dilator are removed leaving the sheath 24 in place. A catheter (or other intravascular instrument) is then inserted through the introducer sheath and threaded down the artery to the desired intravascular location, e.g., the situs of the athrosclerotic occlusion. Once the intravascular procedure (e.g., angioplasty) has been completed, the catheter is removed. Thereafter, the sheath is removed and the surgeon or other trained person applies manual, digital pressure to the percutaneous puncture until hemostasis has occurred.

The closures 200-700 of this invention are each arranged to effect the sealing of the percutaneous (or any other type of puncture, incision, or opening) in the artery or any other tissue separating two portions of the body without necessitating the application of manual, digital pressure thereto. The details of the closures 200-700 will be described later. Suffice it to state for now that each closure is made up of three portions, namely, and anchoring portion arranged to be introduced through the incision or puncture into the artery, a sealing portion arranged to be brought into engagement with the tissue contiguous with the incision and puncture, and a filament portion which is arranged to draw the sealing component toward the anchoring component and into engagement with the tissue contiguous with the opening located opposite to the anchoring component to thereby seal the incision or puncture.

In the embodiment of closure 200 the anchoring portion, sealing portion, and filament portion comprises three individual components, designated by the reference numerals 202, 204, and 206, respectively.

As will be described in detail later once the catheter or intravascular instrument has been removed from the patient's body, but with the introducer sheath 24 left in place, the instrument 20 holding the closure 200 is inserted through the introducer sheath, into the artery 22 and operated to expel the anchoring component 202 of the closure 200 through the opening (e.g., puncture or incision) 26 and into the artery 22. The instrument is then manipulated to draw the anchoring portion 202 into engagement with the inner surface of the arterial tissue contiguous with the incision and puncture 26 and when that is achieved to draw the sealing component 204 into engagement with the outer surface of the arterial tissue contiguous with the incision or puncture (i.e., the tissue surface on the opposite side of that from the anchoring portion) to complete the sealing of the incision or puncture.

Referring now to FIGS. 1-4, the details of instrument 20 will now be described. As can be seen the instrument basically comprises a tubular body 28 in which a plunger assembly is located. The closure 200 is located within a carrier portion 32 (FIG. 2) of the body 28, with the plunger assembly arranged to be operated by the user of the instrument to eject the anchoring component 202 from the carrier portion. The plunger assembly basically comprises a manually operatable plunger actuator 34, a pusher 36, spring biasing means 38, visual indicator means 40, and audible signalling means 42.

The body 28 is a hollow member whose distal end is in the form of a hollow, elongated projection forming the heretofore identified carrier 32. The inside diameter of the carrier is sufficiently large to enable the closure 200 to fit therein, with the anchoring member 202 and sealing member 204 each being oriented longitudinally (See FIG. 2).

As can be seen in FIG. 2, the anchoring component 202 of the closure is located closely adjacent the free end 44 of the carrier 32, while the sealing component 204 is located just proximally of the anchoring component.

The pusher 36 basically comprises an elongated rod-like member, a portion of which extends down the interior of the tubular carrier 32. The outside diameter of the rod 36 is sufficiently small to provide enough clearance between its outer surface and the inner surface of the carrier to enable it to be freely slid down the carrier. The pusher rod 36 has a free or distal end 46 for engaging the sealing component 204 of closure 200 to push it into the anchoring component so that the anchoring component is ejected out of the carrier 32 when the plunger assembly is operated, as will be described later. In the embodiment of FIG. 13 the free end of the pusher rod is configured to engage the anchoring component directly, as will also be described later. A central passageway 48 extends through the pusher rod for passage of the filament component 206 therethrough.

As can be seen clearly in FIG. 3, the free end 44 of the carrier 32 includes a plurality of petal-like, curved projections 50 which are equadistantly spaced about the periphery of the carrier to form a one-way, openable, outlet or gate 52 through which the closure 200 is ejected when the instrument is used.

The carrier 32 is of sufficiently small outside diameter, e.g., 8 French, and is formed of a somewhat flexible material, such as polyethylene or polyvinyl chloride, to enable it to be inserted through the introducer sheath 24 into the artery 22, so that the outlet gate 52 of the carrier is located within the artery. Since the pusher rod 36 extends within the carrier 32 it is also formed of a relatively flexible material, such as polyethylene or polyvinyl chloride. Accordingly, the carrier portion of the instrument with the pusher member therein may be freely passed through the introducer sheath into operative position within the patient's artery, notwithstanding any curvature of the introducer sleeve which may exist.

The proximal end of the instrument's body 28 is in the form of an annularly projecting flange 54. This flange serves as a means for enabling the user to grasp the device 20 with his/her fingers to eject the closure, when desired.

As can be seen in FIGS. 1 and 6, the proximal end of the carrier 32 merges into the instrument's body 28 at a conventional, luer lock 56 to enable the instrument 20 to be releasably secured to a mating luer lock 58 on the proximal end of the introducer sheath 24 when the carrier has been extended through the sheath and into the artery.

The plunger actuator 34 is an elongated member having an enlarged proximal end in the form of a head 60. The distal end of the actuator 34 extends within the hollow interior 62 of the body 28 and has mounted thereon a pair of pinch rollers 64 and a reel 66. The reel 66 serves to hold a portion of the filament component 206 of the closure 200, while the pinch rollers serve as means for engaging portions of that component during the closure placement procedure to ensure that the closure is properly seated within the incision or puncture 26.

The proximal end of the pusher rod 36 is in the form of a disk 68, whose outside diameter is just slightly less than the inside diameter of the space 62 within the instrument's body 28. The disk 68 is disposed immediately adjacent the distal end 70 of the plunger actuator 34.

The plunger actuator 34 is arranged to be slid down the interior 52 of the body 28 from the retracted (inoperative) position shown in FIGS. 1 and 4 to an extended (operative) position shown in FIG. 5 when the plunger assembly is operated. That operation is carried out by the user of the instrument pressing with his/her thumb on the plunger's head 60 while gripping the flange 54 on the instrument's body 28 with his/her fingers. This action causes the pusher rod 36 to be moved down the interior of carrier 32 toward the extended position shown in FIG. 5 against the bias of the biasing means 38. Thus, the free end 70 of the pusher rod 36 engages the sealing member 204 of the closure as shown in FIG. 2 to push it into the anchor member 202, thereby causing the anchor member to move longitudinally down the carrier and through the gate 54 out into the artery like shown in FIG. 5.

As will be described in detail later with reference to FIG. 13, the distal or free end 46 of the pusher rod 36 may be constructed in a different manner from that shown in FIGS. 1–7 to enable it to directly engage the anchor member 202 to push that member out of the gate 52, without using the sealing member 204 as an intermediate force transmitting member. This later embodiment is useful in applications wherein the sealing member 204 is incapable of transmitting a sufficiently strong pushing force through it to eject the anchor member, e.g., in the case where the sealing member is non-rigid such as a collagen powder, gel or some other flowable material disposed within a sack or covering, or has gotten wet to lose its rigidity or force transmitting properties.

The spring biasing means 38 basically comprises an assembly of a spring 72 and a stop 74. The spring 72 is preferrably a helical compression spring, whose outside diameter is just slightly less than the inside diameter of the hollow interior 62 of the instrument's body 28. The stop 74 comprises a fixed ledge which projects radially inwardly from the interior 62 of the instrument's body closely adjacent the luer lock 56. The stop 74 provides a seat for the distal end of the spring.

The spring 72 is interposed between the disk 68 at the proximal end of the pusher rod 38 and the fixed stop 74 and is of a sufficient length that it is slightly compressed when the instrument is in the retracted (inoperative) position shown in FIG. 1. Thus, the spring applies a proximally directed force onto the plunger assembly to tend to hold that assembly in the retracted position.

The visual indicator means 40 basically comprises indicia in the form of a first area 76 of a first color, e.g., red, located on the plunger actuator element 34 at an intermediate point therealong, and a second area 78 of a second color, e.g., green, located on the plunger contiguous with the proximal end of the indicia 76. These two colored areas cooperate with the instrument's body 28 to provide a visual indication of proper operation of the instrument 20, as will be described later.

The audible signalling or indicator means 42 basically comprises a flap 80 projecting radially outward from the plunger rod 36, and a finger 82 projecting proximally longitudinally from the stop 74. The flap and finger are located with respect to each other so that when the plunger assembly is pushed to the extended position wherein the anchoring portion 202 of the closure 200 is ejected from the gate 52 of the carrier and into the artery the finger and flap engage each other whereupon the flap flexes and releases thereby producing an audible sound, e.g., a "click", which indicates that the anchor portion 202 of the closure has been ejected into the artery.

Referring now to FIG. 2, the details of the closure 200 will now be discussed. As can be seen the anchoring component 202 comprises a thin, narrow, strip of material, such as a resorbable lactide/glycolide polymer sold by E.I. DuPont de Nemours, Inc. under the trade designation MEDISORB. The strip is sufficiently rigid such that once it is in position within the artery (as will be described later) it is resistant to deformation to preclude it from bending to pass back through the puncture or incision through which it was first introduced, yet is sufficiently flexible to conform generally to the shape of the interior of the artery so as not to injure the arterial tissue. The anchor strip 202 includes a pair of apertures 202A and 202B located at approximately the middle of the strip and through which apertures a portion of the filament component 206 extends.

The sealing component 204 of the closure 200 basically comprises a pliable plug of any suitable shape, e.g., a brick-like shape. The plug is preferably formed of an absorbent material, such as a resorbable collagen foam, sold by Semex Medical Co.

The filament component 206 of the closure 200 serves to couple the plug component 204 to the anchor component 202 in an arrangement to effect the movement of the plug component (or a portion of it) toward the anchor component, once the anchor component is in its desired position in the artery at the puncture or incision.

The manner of coupling the plug component to the anchor component can be effected in various ways simulating a "pulley" arrangement to achieve any desired "mechanical advantage". A few exemplary arrangements for the filament and other components of the closure are shown in FIGS. 8–12 herein. However, those embodiments are merely exemplary of any number of possible arrangements. Irrespective of the particular embodiment chosen, the filament is preferably formed of resorbable, flexible, strong, material, e.g., a resorbable suture.

In the exemplary embodiment of the closure 200 shown in FIG. 2, one end, i.e., the proximal end, of the filament 206 is reeled up on the storage reel 66. The filament extends off of the reel through the space between pinch rollers 64, down channel 48 in the pusher rod and into a first transverse passageway 204A located adjacent the proximal end of the plug component 204, from there along a portion of the length of the plug component and through a second transverse passageway 204B located adjacent the distal end of the plug component, across the gap separating the anchor component 202 from the plug component 294, in and out of the apertures 202B and 202A, respectively, in the anchor component, and back to the plug component where it passes through passageways 204B and 204A, respectively, and terminates in a knot or other protrusion 206A adjacent the point at which it exits from passageway 204A.

Operation of the instrument 20 is best understood by reference to FIGS. 4–7 and is as follows: the instrument 20 is inserted within the introducer sheath 29 so that the free end 44 of the tubular carrier member 32 extends through the puncture or incision 26 like that shown in FIG. 4. The instrument 20 is then secured to the sheath 24 by coupling their luer locks 56 and 58 together. The user then engages and pushes on the cap 60 of the plunger actuator 34 with his/her thumb, while grasping the flange 54 of the tubular body member 28 between his/her fingers. This action slides the plunger actuator 34 and the pusher rod in the distal direction within the instrument, whereupon the free end 70 of the pusher rod engages the proximal end of the plug component 204 of the closure 200. Continued pressing of the plunger actuator into the body forces the closure to slide down the interior of the carrier towards the outlet gate 52. At the point that the finger 82 engages the flap 80 to produce the audible "click" the pusher rod 36 will have pushed the anchor member 202 out through the instrument's outlet gate 52 and into the interior of the artery as shown in FIG. 5. At this time the plug component 204 will still be within the carrier 32, but now located closely adjacent the outlet gate 52.

Upon hearing the "click" the operator releases the pressure on the plunger actuator cap 60, whereupon the spring 72 carries the plunger actuator 34 and pusher rod 36 in the proximal direction. The pinch rollers 64 grasp the filament component 206 between them with sufficient force so that movement of the actuator member 34 in the proximal direction pulls the filament 206 in that direction. Since the filament extends longitudinally through the passageway 48 in the pusher rod 36 and through the the plug component 204 to the anchor component 202, the pulling of the filament in the proximal direction pulls the anchor component 204 into engagement with the distal end 44 of the carrier 32. The petals 50, being curved slightly inward (See FIG. 2), tend to prevent the anchor component 204 from gaining ingess back into the carrier so that it becomes "trapped" on the free end of the carrier by the proximally directed pulling force exerted through the filament component. This action is shown clearly in FIG. 6.

The trapping of the anchor component at the distal end of the carrier is indicated to the user by the visual indication means 40. In this regard when the anchor component 204 is against the free end of the carrier as shown in FIG. 6 the plunger actuator will have moved to the longitudinal position with respect to the instrument's body 28 so that only the green indicia 78 will be visible. If, however, the anchor component was pulled back into the carrier the plunger actuator will have been able to move further proximally with respect to the body 28, whereupon the red indicia 76 will be visible. This indicates improper placement, and that the closure is not ready to seal the incision or puncture.

Assuming that the anchor component 202 is in the proper position, i.e., it is against the distal end 44 of the carrier 32, the entire instrument 20 (and the introducer sheath which is connected to the engaging luer locks 56 and 58) is pulled in the proximal direction. This pulling action brings the anchor component 202 into engagement with the tissue of the interior of the artery contiguous with the incision or puncture 26. Further pulling on the instrument in the proximal direction effectively pulls on the filament component in the proximal direction (the anchor component cannot move since it is now in abutment with the interior tissue of the artery contiguous with the incision or puncture). Accordingly, the filament slips through the openings in the anchoring portion and the plug components until its knot 206C engages the plug portion contiguous with passageway 204A. The knot is sufficiently large so that it doesn't pass into the passageway 204A. Accordingly, further pulling on the filament in the proximal direction causes the plug component 204 to be pulled out of the carrier's gate and into the body of the patient outside of the artery. Continued pulling on the instrument in the proximal direction causes the knot 206A on the filament to move closer to the anchoring component. This causes the plug component to deform, e.g., fold it in two, and move towards the anchor component until the plug component engages the tissue contiguous with the incision or puncture on the opposite side thereof from the anchor component as shown in FIG. 7. This action effectively seals the incision or puncture.

The presence of blood or other liquid at the situs of the closure causes the plug to expand somewhat, thereby holding the filament frictionally within the passageways 204A and 204B so that the filament cannot slip with respect to the anchor and plug components. Accordingly, the tissue contiguous with the puncture or incision will be securely clamped between the anchor component and the plug component and will remain such even when the proximal pulling force is removed.

After the opening has been sealed the instrument and the accompanying introducer sheath are completely removed, and the proximal end of the filament is secured in place on the patient's skin, such as by use of adhesive tape.

With the closure in position the anchor portion 202 (the only portion within the artery) does not take up a substantial portion of the interior of the artery and thus does not block off or otherwise impede the flow of blood therethrough. Since the components of the closure are all formed of resorbable materials the closure can be left in place within the body until it is absorbed.

When the closure 200 of the subject invention is used to hemostatically seal a puncture or incision in an artery or other vessel, in order to minimize the risk of thrombosis the anchor component (the only component which is exposed to the flow of blood through the artery) may be coated with a non-thrombogenic material. Such a material can comprise a waxy coating, such as coconut oil, etc. Moreover, when the closure of this invention is used for sealing punctures or incisions in arteries a conventional clotting agent, such as tissue thromboplastin may be provided in the closure to accelerate hemostasis.

As should be appreciated by those skilled in the art the plural sections of the filament 206 between the anchor component 202 and the plug component 204 effectively form a "pulley" arrangement to increase the mechanical advantage of the force applied to the filament to move the two components toward each other. Accordingly, the closure can be properly seated without the application of a high pulling force. The use of the pinch rollers 64 ensures that irrespective of how hard the instrument is withdrawn from the opening 26, the amount of force applied to the filament 206 will not exceed a predetermined maximum, e.g., one pound. This feature is of considerable importance to ensure that the anchor portion of the closure is not pulled through the opening (e.g., incision or puncture) once it is in place.

The embodiment of the closure 200 shown in FIG. 2 provides a mechanical advantage of double the force applied to the filament since there are two sections of the filament 206 located between the anchoring component 202 and the plug component 204.

The embodiment of the closure 400 shown in FIG. 9 also provides a mechanical advantage of two. As can be seen in FIG. 9 the closure 400 is substantially similar in construction to closure 200 and hence the common features thereof will be given the same reference numbers. The difference in construction between closures 400 and 200 is that the closure 400 includes two longitudinally extending passageways 400A and 400B through which the filament extends instead of the two transverse passageways 200A and 200B of the closure 200.

The closure 500 of FIG. 10 also provides a mechanical advantage of two and is similar in construction to closure 400 except that it only includes one longitudinally extending passageway 500A. Thus the common features of the closures 500 and 400 are given the same reference numbers.

In the embodiment of closure 600 shown in FIG. 11 a mechanical advantage of four is provided since there are four sections of the filament 206 located between the anchoring component 202 and the plug component 204. As can be seen in FIG. 11 the closure 600 is substantially similar in construction to closure 400 and hence the common features thereof will be given the same reference numbers. The difference in construction between closures 600 and 400 is that the plug component of the closure 600 also includes one transverse passageway 600A through which the filament extends, and the anchor component includes two additional passageways 600C and 600D through which the filament extends.

In the embodiment of closure 700 shown in FIG. 12 a mechanical advantage of three is provided since there are three sections of the filament 206 located between the anchoring component 202 and the plug component 204. As can be seen in FIG. 12 the closure 700 is substantially similar in construction to closure 400 and hence the common features thereof will be given the same reference numbers. The difference in construction between closures 700 and 400 is that the plug component of the closure 700 includes one additional longitudinal passageway 700C through which the filament extends, and the anchor component includes one additional passageways 200C through which the filament extends.

In FIG. 8 there is shown a closure 300 which, like the closures 200, 400, and 500 provides a mechanical advantage of two. However, unlike closures 200, 400, and 500 the closure 300 is formed as an integral unit. Thus, there are no separate anchoring component and plug component. Instead the anchoring component 302 is the distal end portion of the closure, while the plug component 304 is the proximal end portion of the closure. The filament 206 extends through two longitudinal extending passageways 304A and 304B in the plug portion and through two openings 302A and 302B in the anchor portion in the same manner as that of the closure 400. Operation of the closure 300 is substantially the same as described heretofore. Accordingly, when the anchor portion 302 is in place against the inner surface of the artery 22 contiguous with the opening 26 and the filament 206 is pulled distally, the plug portion 304 will be deformed and portions of it drawn toward the anchoring portion to sandwich the arterial tissue contiguous with the incision or puncture therebetween.

In FIG. 13 there is shown an alternative embodiment of the free or distal end 46 of the pusher rod 36. In that embodiment the distal end of the pusher rod 36 has attached thereto of a hollow cylinder 100 having a sidewall 102. The sidewall includes an annular recess 104 in its inner periphery into which is received an annular flange 106 extending about the free end 46 of the pusher rod 36. The passageway 48 extending through the pusher rod communicates with the interior of the cylinder 100. The plug component 204 of the closure 200 is disposed within the cylinder 100 and the filament 206 extends through the passageway 48 back to the reel 66, as described heretofore.

The outside diameter of the pusher's cylindrical sidewall 102 is selected so that when the plug component is within the cylinder 100 the free end 108 of the cylinder's sidewall 102 will directly engage some portion of the end 202E of the anchor component 202. Accordingly, the pushing force to eject the anchor component will be applied directly to the anchor component 202 and without any force having to be transmitted through the plug component 204. This arrangement is of particular utility in applications wherein the absorption of liquid by the closure's plug component would reduce its ability to transmit a pushing force therethrough. Moreover, this alternative embodiment of the pusher rod is useful for application wherein the closure is constructed so that its plug portion is not rigid, e.g., is in the form of a sack or bag of some flexible material and which is filled with an absorbent flowable material, such as a collagen powder, a hemostatic gel, etc.

As should be appreciated from the foregoing, the closures 200-700 and introducing instrument 20 of the subject invention and their method of use enables the ready, effective and efficient sealing of an opening, such as a puncture or incision in a body organs or tissue, be it a blood vessel, a lumen, a duct, etc. For example, the closure and its method of use can be used for the purpose of sealing percutaneous transhepatic punctures to preclude the risk of bile leakage into the peritoneum, via the liver puncture site. Moreover, the closure, instruments and their method of use can be used for sealing percutaneous incisions in the lung or heart, such as could result from a wound.

Without further elaboration the foregoing will so fully illustrate our invention that others may, by applying current or future knowledge, adopt the same for use under various conditions of service.

What is claimed is:

1. An instrument for sealing an opening in tissue separating one portion of the body of a living being from another portion thereof, said instrument comprising carrier means for receipt of closure means, said closure means being arranged to be expelled from said carrier means, said carrier means comprising tubular means having a proximally located portion and a distally located portion, said distally located portion having a free end arranged to be introduced through said opening, said closure means comprising anchoring means, sealing means, and filament means, said anchoring means including a tissue engaging portion configured to pass through said opening in one direction but resistant to passage therethrough in the opposite direction, said sealing means including a tissue engaging portion, said filament means being connected between said anchoring means and said sealing means and comprising a first portion and a second portion, said instrument being arranged to expel said anchoring means through said opening and to draw said tissue engaging portion of said anchoring means into engagement with the tissue contiguous with said opening, said first portion of said filament means being arranged to be drawn in the proximal direction by a force applied thereto, whereupon said second portion of said filament means causes said tissue engaging portion of said sealing means to move with respect to said anchoring means and into engagement with the tissue contiguous with said opening on the opposite side thereof from said anchoring means, whereupon said tissue engaging portion of said sealing means seals said opening from the flow of fluid therethrough.

2. The instrument of claim 1 wherein said carrier means comprises tubular means and ejecting means, said tubular means having a free end with said said closure being located in said tubular means adjacent said free end, said free end of said tubular means being arranged to be extended through said opening, said ejecting means being arranged to move from a first position to a second position for pushing said anchoring means out of said free end of said tubular means but leaving said sealing means within said tubular means, whereupon said instrument may be operated to draw said tissue engaging portion of said anchoring means into engagement with the tissue contiguous with said opening.

3. The instrument of claim 2 additionally comprising first indicator means to provide a first signal that said anchoring means has been pushed out of said free end of said tubular means.

4. The instrument of claim 3 wherein said first signal is audible.

5. The instrument of claim 2 additionally comprising retraction means for retracting said anchoring means to a predetermined position with respect to the free end of said tubular means.

6. The instrument of claim 5 wherein said free end of said tubular means comprises a one-way gate enabling said anchoring means to pass therethrough in one direction but precluding it from passing back therethrough in the opposite direction.

7. The instrument of claim 6 wherein said one-way gate comprises plural, flexible petal-like members.

8. The instrument of claim 5 wherein said retraction means comprises spring biased means coupled to said ejecting means for moving said ejecting means back toward said first position.

9. The instrument of claim 5 whereupon when said anchoring means is in said predetermined position said free end of said tubular portion of said instrument may be withdrawn through said opening to draw said tissue engaging portion of said anchoring means into engagement with the tissue contiguous with said opening, whereupon further withdrawl of said tubular portion of said instrument effects the drawing of said second portion of said filament means in the proximal direction to cause said tissue engaging portion of said sealing means to move with respect to said anchoring means and into engagement with the tissue contiguous with said opening on the opposite side thereof from said anchoring means to seal said opening.

10. The instrument of claim 9 wherein said retraction means comprises spring biased means coupled to said ejecting means for moving said ejecting means back toward said first position.

11. The instrument of claim 9 additionally comprising second indicator means for providing a second signal that said anchoring means is located against the free end of said tubular means.

12. The instrument of claim 11 wherein said second signal is visible.

13. The instrument of claim 11 additionally comprising first indicator means to provide a first signal that said anchoring means has been pushed out of said free end of said tubular means.

14. The instrument of claim 13 wherein said first signal is audible.

15. The instrument of claim 9 additionally comprising force limiting means for prevent a force in excess of a predetermined maximum value from being applied to said filament means when said second portion of said filament means is drawn in the proximal direction.

16. The instrument of claim 15 wherein said force limiting means comprises a pair of pinch rollers between which said second portion of said filament means passes.

17. The instrument of claim 16 wherein said ejecting means comprises a plunger and wherein said pinch rollers are mounted on said plunger.

18. The instrument of claim 17 wherein said second portion of said filament means is wound on a reel and said reel is mounted on said plunger.

19. The instrument of claim 18 wherein said retraction means comprises spring biased means coupled to said plunger for moving said plunger back toward said first position.

20. The instrument of claim 19 additionally comprising first indicator means to provide a first signal that said anchoring means has been pushed out of said free end of said tubular means.

21. The instrument of claim 20 wherein said first signal is audible.

22. The instrument of claim 20 additionally comprising second indicator means for providing a second signal that said anchoring means is located against the free end of said tubular means.

23. The instrument of claim 22 wherein said second signal is visible.

24. The instrument of claim 1 wherein said first and second portions of said filament means are coupled together in an arrangement to increase the mechanical advantage of said force applied to said second portion of said filament means.

25. The instrument of claim 24 wherein said arrangement comprises an intermediate portion of said filament means extending from said first portion thereof through a first portion of said anchoring means and back through a second portion of said anchoring means towards said sealing means.

26. The instrument of claim 25 wherein said intermediate portion of said filament means is looped through at least three portions of said anchoring means.

27. The instrument of claim 25 wherein said intermediate portion of said filament means is looped through at least four portions of said anchoring means.

28. The instrument of claim 25 wherein said anchoring means and said sealing means are separate members.

29. The instrument of claim 25 wherein said anchoring means and said sealing means are an integral member.

30. The instrument of claim 25 wherein said closure means is formed of an absorbable material.

31. The instrument of claim 24 wherein said anchoring means and said sealing means are separate members.

32. The instrument of claim 24 wherein said anchoring means and said sealing means are an integral member.

33. The instrument of claim 24 wherein said closure means is formed of an absorbable material.

34. A closure for sealing an opening in tissue separating one portion of the body of a living being from another portion thereof to prevent the flow of bodily fluid from said one portion to said other portion through said opening, said closure being arranged to be inserted into said opening by an instrument comprising carrier means, said carrier means comprising tubular means having a proximally located portion and a distally located portion, said distally located portion having an open free end arranged to be introduced through said opening, said closure comprising anchoring means, sealing means, and filament means, said anchoring means including a tissue engaging portion configured to pass through said opening in one direction but resistant to passage therethrough in the opposite direction, said sealing means including a tissue engaging portion, said filament means being connected between said anchoring means and said sealing means and comprising a first portion and a second portion, said first portion of said filament means being arranged to be drawn in one direction after said anchoring means is inserted through said opening, whereupon said second portion of said filament means causes said tissue engaging portion of said sealing means to move with respect to said anchoring means and into engagement with the tissue contiguous with said opening on the opposite side thereof from said anchoring means, whereupon said tissue engaging portion of said sealing means seals said opening from the flow of fluid therethrough.

35. The closure of claim 34 wherein said first and second portions of said filament means are coupled together in an arrangement to increase the mechanical advantage of said force applied to said second portion of said filament means.

36. The closure of claim 35 wherein said arrangement comprises an intermediate portion of said filament means extending from said first portion thereof through a first portion of said anchoring means and back through a second portion of said anchoring means towards said sealing means.

37. The closure of claim 36 wherein said intermediate portion of said filament means is looped through at least three portions of said anchoring means.

38. The closure of claim 36 wherein said intermediate portion of said filament means is looped through at least four portions of said anchoring means.

39. The closure of claim 35 wherein said anchoring means and said sealing means are separate members.

40. The closure of claim 35 wherein said anchoring means and said sealing means are an integral member.

41. The closure of claim 35 wherein said closure means is formed of an absorbable material.

42. The closure of claim 34 wherein said anchoring means and said sealing means are separate members.

43. The closure of claim 34 wherein said anchoring means and said sealing means are an integral member.

44. The closure of claim 34 wherein said closure means is formed of an absorbable material.

45. A method of using an instrument to seal a small opening in tissue separating one portion of the body of a living being from another portion thereof, said instrument comprising carrier means, and closure means, said carrier means comprising a tubular member having a distally located portion having a free end, said closure means comprising anchoring means, sealing means, and filament means, said anchoring means including a tissue engaging portion configured to pass through said opening in one direction but resistant to passage therethrough in the opposite direction, said sealing means including a tissue engaging portion, said filament means being connected between said anchoring means and said sealing means and comprising a first portion and a second portion, said method comprising locating said closure within said carrier means adjacent the free end thereof, introducing said free end of said carrier means through said opening, expelling said anchoring means of said closure from said free end of said carrier means, drawing said tissue engaging portion of said anchoring means into engagement with the tissue contiguous with said opening, and applying a drawing force on said first portion of said filament means to cause said second portion of said filament means to move said sealing means out of said carrier means, whereupon said tissue engaging portion of said sealing means moves with respect to said anchoring means and into engagement with the tissue contiguous with said opening on the opposite side thereof from said anchoring means so that said tissue engaging portion of said sealing means seals said opening from the flow of fluid therethrough.

46. The method of claim 45 additionally comprising the step of providing a signal that said anchoring means has been expelled from said carrier means.

47. The method of claim 46 wherein after said anchoring means has been expelled from said carrier means then drawing said anchoring means into a predetermined position with respect to said free end of said carrier means to hold it in said position prior to drawing said tissue engaging portion of said anchoring means into engagement with the tissue contiguous with the opening.

48. The method of claim 46 wherein after said anchoring means has been expelled from said carrier means then drawing said anchoring means into a predetermined position with respect to said free end of said carrier means to hold it in said position prior to drawing said tissue engaging portion of said anchoring means into engagement with the tissue contiguous with the opening.

49. The method of claim 47 additionally comprising the step of providing a signal that said anchoring portion is in said predetermined position.

50. The method of claim 48 additionally comprising the step of providing a signal that said anchoring portion is in said predetermined position.

51. The method of claim 45 additionally comprising coupling said first and second portions of said filament means together in an arrangement to increase the mechanical advantage of said drawing force.

52. The method of claim 45 additionally comprising coupling said first and second portions of said filament means together in an arrangement to increase the mechanical advantage of said drawing force.

53. The method of claim 45 additionally comprising automatically ensuring that said drawing force does not exceed a predetermined maximum value.

54. The method of claim 48 additionally comprising coupling said first and second portions of said filament means together in an arrangement to increase the mechanical advantage of said drawing force.

55. The method of claim 54 additionally comprising automatically ensuring that said drawing force does not exceed a predetermined maximum value.

* * * * *